US012636314B1

(12) United States Patent
Smith et al.

(10) Patent No.: US 12,636,314 B1
(45) Date of Patent: May 26, 2026

(54) ZINC OXIDE FORMULATION AND ASSOCIATED APPLICATOR AND PACKAGING SYSTEM

(71) Applicant: Sage Products, LLC, Cary, IL (US)

(72) Inventors: Lori Beth Smith, Lake In The Hills, IL (US); Theresa Sebastian, Chicago, IL (US); Brett Blabas, Naperville, IL (US); Claire McCauley, Chicago, IL (US)

(73) Assignee: Sage Products, LLC, Cary, IL (US)

( * ) Notice: Subject to any disclaimer, the term of this patent is extended or adjusted under 35 U.S.C. 154(b) by 57 days.

(21) Appl. No.: 17/963,326

(22) Filed: Oct. 11, 2022

Related U.S. Application Data

(60) Provisional application No. 63/254,818, filed on Oct. 12, 2021.

(51) Int. Cl.
| | |
|---|---|
| *A61K 33/30* | (2006.01) |
| *A61K 9/70* | (2006.01) |
| *A61K 31/718* | (2006.01) |
| *A61K 47/44* | (2017.01) |

(52) U.S. Cl.
CPC ............ *A61K 33/30* (2013.01); *A61K 9/7007* (2013.01); *A61K 31/718* (2013.01); *A61K 47/44* (2013.01)

(58) Field of Classification Search
CPC .... A61K 9/7007; A61K 33/30; A61K 31/718; A61K 47/44; A61F 2013/530605; B29D 7/01
See application file for complete search history.

(56) References Cited

U.S. PATENT DOCUMENTS

| | | | | |
|---|---|---|---|---|
| 3,929,135 | A | * | 12/1975 | Thompson ................ B32B 3/28 604/374 |
| 5,439,628 | A | * | 8/1995 | Huang ........................ C08J 5/18 425/363 |
| 7,455,849 | B2 | * | 11/2008 | Utschig .................. A61Q 19/00 424/401 |
| 7,888,547 | B2 | * | 2/2011 | Masini .................. A61F 15/001 604/304 |

| | | | | |
|---|---|---|---|---|
| 2003/0082219 | A1 | * | 5/2003 | Warren ............. A61F 13/51305 514/23 |
| 2003/0190371 | A1 | * | 10/2003 | Graaf ...................... A61K 8/27 424/642 |
| 2007/0009472 | A1 | * | 1/2007 | Niebauer ............. A61Q 17/005 424/70.28 |
| 2007/0104806 | A1 | * | 5/2007 | Seiberg .................. A61K 36/45 424/769 |
| 2020/0281779 | A1 | * | 9/2020 | Kalentun ............. A61F 13/472 |

FOREIGN PATENT DOCUMENTS

JP        H1029932 A  *  2/1998

OTHER PUBLICATIONS

Carede "What is Laminated Tissue Paper with PE Film?", Aug. 19, 2919, https://www.czcarede.com/what-is-laminated-tissue-paper-with-pe-film/ (accessed Nov. 30, 2023). (Year: 2019).*
Busch "Phenoxyethanol", Apr. 8, 2020, https://puracy.com/blogs/ingredients/phenoxyethanol (accessed May 16, 2024). (Year: 2020).*
Medline Industries, LP, Drug Label Information for Medline Remedy Essentials—white petrolatum, zinc oxide paste, taken from https://dailymed.nlm.nih.gov/dailymed/drugInfo.cfm?setid=42a033d6-782b-2d7f-e054-00144ff8d46c, dated Oct. 4, 2021, 6 pages.
Sage Products, LLC, Drug Label Information for Comfort Shield Barrier—dimethicone cloth, taken from https://dailymed.nlm.nih.gov/dailymed/drugInfo.cfm?setid=cc08f571-84ae-4c2f-b09d-a83a8efc39f5, dated Feb. 22, 2022, 10 pages.
Smith Nephew, Inc., Viscopaste* PB7 Zinc Paste Bandage, taken from https://www.woundsource.com/print/product/viscopaste-pb7-zinc-paste-bandage, available at least as early as Jul. 29, 2021, 3 pages.
Sage Products, LLC, Incontinence Care, https://sageproducts.com/wp-content/uploads/Incontinence-Care-Brochure.pdf, dated Jan. 1, 2017, 8 pages.

* cited by examiner

*Primary Examiner* — Bethany P Barham
*Assistant Examiner* — Judith Marie Kamm
(74) *Attorney, Agent, or Firm* — Foley & Lardner LLP

(57)        ABSTRACT
A formulation for treating incontinence-associated dermatitis or other skin conditions includes zinc oxide as an active pharmaceutical ingredient, a starch as a rheology modifier, a preservative or preservative system, an emulsifier, an emollient, and a water solvent. An applicator for applying a formulation to an affected area on a patient includes a sheet of a cloth material. The sheet is non-permeable such that a first side of the sheet is provided with the zinc oxide formulation and a second opposite side of the sheet is not exposed to the zinc oxide formulation.

19 Claims, 8 Drawing Sheets

| INGREDIENT | | POTENTIAL USAGE RANGE (%) | |
|---|---|---|---|
| INCI NAME(S) | FUNCTION | LOW | HIGH |
| ZINC OXIDE | API | 5 | 25 |
| PHENOXYETHANOL | PRESERVATIVE | 0.4 | 1.2 |
| BENZOIC ACID | PRESERVATIVE | 0.4 | 1.2 |
| DEHYDROACETIC ACID | PRESERVATIVE | 0.4 | 1.2 |
| ETHYLHEXYLGLYCERIN | PRESERVATIVE | 0.4 | 1.2 |
| BETULIN | PRESERVATIVE | 1 | 10 |
| TRI(POLYGLYCERYL-3/LAURYL) HYDROGENATED TRILINOLEATE | EMULSIFIER | 0.5 | 3.5 |
| GLYCERYL STEARATE/PEG-100 STEARATE | EMULSIFIER | 2 | 10 |
| HYDROXYETHYLCELLULOSE | RHEOLOGY MODIFIER | 0.2 | 2.5 |
| HYDROXYPROPYL STARCH PHOSPHATE | RHEOLOGY MODIFIER | 0.5 | 6.5 |
| ISOPROPYL PALMITATE | EMOLLIENT | 1 | 5 |
| DICAPRYLYL CARBONATE | EMOLLIENT | 1 | 30 |
| BEESWAX | EMOLLIENT | 0.5 | 6 |
| LANOLIN | EMOLLIENT | 0.5 | 3 |
| CETEARYL ETHYLHEXANOATE | EMOLLIENT | 1 | 8 |
| ISOPROPYL MYRISTATE | EMOLLIENT | 1 | 8 |
| DIMETHICONE | EMOLLIENT | 0.5 | 1 |
| STEARYL ALCOHOL | EMOLLIENT | 0.5 | 5 |
| CETYL ALCOHOL | EMOLLIENT | 0.5 | 5 |
| BISABOLOL | EMOLLIENT | 0.1 | 2 |
| AQUA (WATER) | SOLVENT | 40 | 80 |
| PROPYLENE GLYCOL | SOLVENT | 0.5 | 8 |
| METHYL PROPANEDIOL | SOLVENT | 0.5 | 10 |
| ALOE BARBADENSIS LEAF | MOISTURIZER | 1 | 10 |
| GLYCERIN | HUMECTANT | 1 | 20 |
| MALTODEXTRIN | FILM-FORMER | 0.5 | 2.5 |
| DISODIUM COCOAMPHODIACETATE | SURFACTANT | 1 | 30 |
| COCAMIDE DEA | SURFACTANT | 1 | 30 |

BACK

FRONT

920

1000

900

910a

900

910b

900

910c

900

910d

900

ZINC OXIDE FORMULATION AND ASSOCIATED APPLICATOR AND PACKAGING SYSTEM

CROSS-REFERENCE TO RELATED APPLICATIONS

This application claims the benefit of and priority to U.S. Provisional Application No. 63/254,818, filed on Oct. 12, 2021, which is hereby incorporated by reference herein in its entirety.

BACKGROUND

The present disclosure relates generally to a zinc oxide formulation and a cloth delivery device comprising the same for treating incontinence-associated dermatitis (IAD) and moisture associated skin damage (MASD).

Incontinence-associated dermatitis (IAD) is a common problem for patients who are bedridden and incontinent. Current products on the market for IAD and MASD treatment consist of a formulation that contains zinc oxide, petrolatum, and/or dimethicone. Formulations utilizing zinc oxide may also be used to treat other forms of dermatitis, diaper rash, minor burns, severely chapped skin, or other skin irritations. Typically, the formulations are thick pastes, which makes application to and removal from a patient's skin difficult and potentially painful for the patient, and may result in damaging the skin further. Furthermore, the opaque formulation does not allow the clinician or user to assess the patient's skin throughout care and treatment.

In addition, the current zinc oxide formulations are messy, both for the clinician and the patient, largely in part due to the high levels of petrolatum, which changes properties, such as viscosity (i.e., thins) when exposed to normal and raised body temperatures. Further, current methods of the delivery of zinc oxide, either via a tube or spray, are also messy and do not allow the clinician to know how much of the formulation has been applied. Zinc oxide formulations packaged in tubes require clinicians to either twist or pop a cap to access the formulation, and squeezing a tube to dispense the formulation may be difficult due to its thickness. The cap must also be replaced after use, which may be difficult or messy if the clinician's hospital glove is soiled due to formulation application.

The present disclosure seeks to overcome certain of these limitations and other drawbacks of existing zinc oxide formulations and devices for delivering the same, for treating incontinence-associated dermatitis and other skin irritations, and to provide new features that are not heretofore available.

BRIEF DESCRIPTION OF THE DRAWINGS

FIG. 1 is a list of potential ingredients for a zinc oxide formulation, according to an exemplary embodiment.

DETAILED DESCRIPTION

Figure 2:
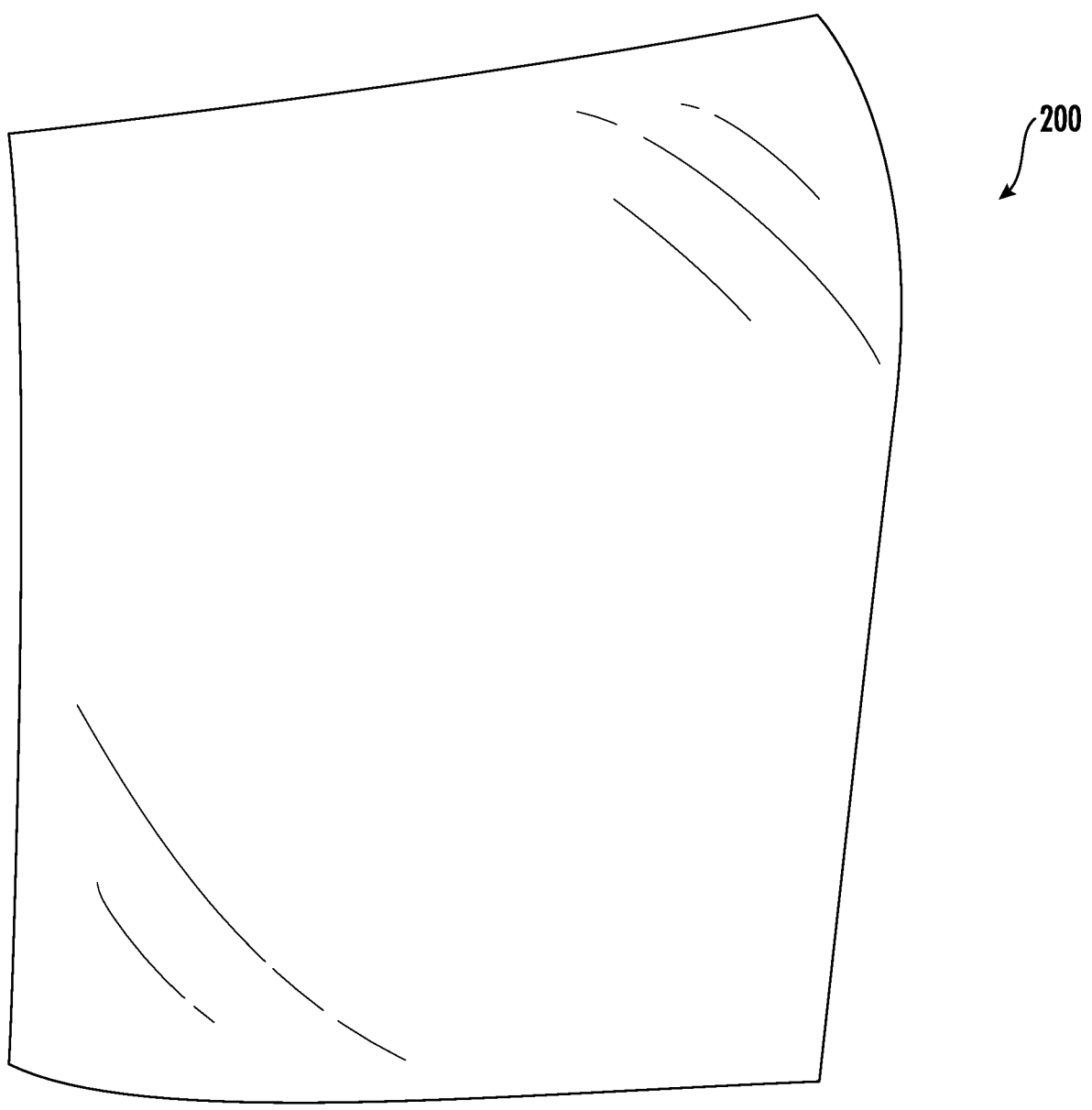
FIG. 2 shows a cloth applicator for a zinc oxide formulation, according to an exemplary embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

It is to be appreciated that certain aspects, modes, embodiments, variations and features of the present methods are described below in various levels of detail in order to provide a substantial understanding of the present technology. It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a preservative" includes a combination of two or more preservatives, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, 10%, or 20% in either direction (greater than or less than) of the number unless otherwise stated or otherwise evident from the context (except where such number would be less than 0% or exceed 100% of a possible value).

As used herein, the terms "subject", "patient", or "individual" can be an individual organism, a vertebrate, a mammal, or a human. In some embodiments, the subject, patient or individual is a human.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

Formulation

In one aspect, the present disclosure provides a topical formulation comprising an active pharmaceutical ingredient (API) for treating and/or protecting the skin of a patient. In an exemplary embodiment, the formulation also includes a preservative or preservative system ("preservative"), an emulsifier, a rheology modifier, an emollient, and a solvent in the form of water. In some embodiments, the formulation includes one or more of the following optional ingredients: a moisturizer, a humectant, a film-former, a surfactant, and/or an additional solvent for the preservative or preservative system.

The formulation enables a simplified delivery to the patient's skin via a cloth. Compared to current zinc oxide formulations on the market, the formulation of the present disclosure may provide a softer, smoother texture that would reduce the amount of force needed to apply to/remove from skin, thus reducing the risk of further skin damage. The formulation may also be less opaque, allowing the clinician to assess the patient's skin, while still being occlusive and providing a protective barrier.

FIG. 1 lists several possible ingredients, their function, and potential usage levels that may be present in the formulation. A formulation according to the present disclosure may include any number of and any combination of the ingredients listed in FIG. 1.

Referring to FIG. 1, in an exemplary embodiment, the active pharmaceutical ingredient (API) is zinc oxide. In some embodiments, the formulation comprises about 5 wt % to about 25 wt % zinc oxide. In some embodiments, the formulation comprises about 5 wt % to 10 wt %, about 10 wt % to 15 wt %, about 15 wt % to 20 wt %, or about 20 wt % to about 25 wt % of the active pharmaceutical ingredient, such as zinc oxide.

Still referring to FIG. 1, in some embodiments, the preservative is selected from the group consisting of phenoxyethanol, benzoic acid, dehydroacetic acid, ethylhexylglycerin, betulin, and a combination of any two or more thereof. In some embodiments, the formulation comprises about 0.4 wt % to about 10 wt % preservative. In some embodiments, the formulation comprises about 0.4 wt % to 1.0 wt %, about 1.0 wt % to 2.0 wt %, about 2.0 wt % to 3.0 wt %, about 3.0 wt % to 4.0 wt %, about 4.0 wt % to 5.0 wt %, about 5.0 wt % to 6.0 wt %, about 6.0 wt % to 7.0 wt %, about 7.0 wt % to 8.0 wt %, about 8.0 wt % to 9.0 wt %, or about 9.0 wt % to 10 wt % preservative. In some exemplary embodiments, the formulation comprises about 0.4 wt % to 1.2 wt % or about 1 to 10 wt % preservative. In some exemplary embodiments, the formulation comprises about 0.4 wt % to 1.2 wt % phenoxyethanol, benzoic acid, dehydroacetic acid, and/or ethylhexylglycerin, or about 1 to 10 wt % betulin.

Still referring to FIG. 1, in some embodiments, the emulsifier is selected from the group consisting of tri (polyglyceryl-3/lauryl) hydrogenated trilinoleate, glyceryl stearate, PEG-100 stearate, and a combination of any two or more thereof. In some embodiments, the formulation comprises about about 0.5 wt % to about 10 wt % emulsifier. In some embodiments, the formulation comprises about 0.5 wt % to 1.0 wt %, about 1.0 wt % to 2.0 wt %, about 2.0 wt % to 3.0 wt %, about 3.0 wt % to 4.0 wt %, about 4.0 wt % to 5.0 wt %, about 5.0 wt % to 6.0 wt %, about 6.0 wt % to 7.0 wt %, about 7.0 wt % to 8.0 wt %, about 8.0 wt % to 9.0 wt %, or about 9.0 wt % to 10 wt % emulsifier. In some exemplary embodiments, the formulation comprises about 0.5 wt % to 3.5 wt % or about 2 wt % to 10 wt % emulsifier. In some exemplary embodiments, the formulation comprises about 0.5 wt % to 3.5 wt % tri (polyglyceryl-3/lauryl) hydrogenated trilinoleate or about 2 wt % to 10 wt % glyceryl stearate/PEG-100 stearate.

Still referring to FIG. 1, in some embodiments, the rheology modifier is selected from the group consisting of hydroxyethylcellulose, hydroxypropyl starch phosphate, and the combination thereof. In some embodiments, the formulation comprises about 0.2 wt % to about 6.5 wt % rheology modifier. In some embodiments, the formulation comprises about 0.2 wt % to 1.0 wt %, about 1.0 wt % to 2.0 wt %, about 2.0 wt % to 3.0 wt %, about 3.0 wt % to 4.0 wt %, about 4.0 wt % to 5.0 wt %, about 5.0 wt % to 6.0 wt %, or about 6.0 wt % to 6.5 wt % rheology modifier. In some exemplary embodiments, the formulation comprises about 0.2 wt % to 2.5 wt % or about 0.5 wt % to 6.5 wt % rheology modifer. In some exemplary embodiments, the formulation comprises about 0.2 wt % to 2.5 wt % hydroxyethylcellulose or about 0.5 wt % to 6.5 wt % hydroxypropyl starch phosphate.

Still referring to FIG. 1, in some embodiments, the emollient is selected from the group consisting of bisobolol, dimethicone, lanolin, stearyl alcohol, cetyl alcohol, beeswax, isopropyl palmitate, cetearyl ethylhexanoate, isopropyl myristate, dicaprylyl carbonate, and a combination of any two or more thereof. In some embodiments, the formulation comprises about 0.1 wt % to about 30 wt % emollient. In some embodiments, the formulation comprises about 0.1 wt % to 1.0 wt %, about 1 wt % to 5 wt %, about 5 wt % to 10 wt %, about 10 wt % to 15 wt %, about 15 wt % to 20 wt %, about 20 wt % to about 25 wt %, or about 25 wt % to about 30 wt % emollient. In some exemplary embodiments, the formulation comprises about 0.1 wt % to 2.0 wt %, about 0.5 wt % to 1.0 wt %, about 0.5 wt % to 3.0 wt %, about 0.5 wt % to 5.0 wt %, about 0.5 wt % to 6.0 wt %, about 1.0 wt % to 5.0 wt %, about 1.0 wt % to 8.0 wt %, or about 1.0 wt % to 30 wt % emollient. In some exemplary embodiments, the formulation comprises about 0.1 wt % to 2.0 wt % bisabolol, or about 0.5 wt % to 1.0 wt % dimethicone, or about 0.5 wt % to 3.0 wt % lanolin, or about 0.5 wt % to 5.0 wt % stearyl alcohol and/or cetyl alcohol, or about 0.5 wt % to 6.0 wt % beeswax, or about 1.0 wt % to 5.0 wt % isopropyl palmitate, or about 1.0 wt % to 8.0 wt % cetearyl ethylhexanoate and/or isopropyl myristate, or about 1.0 wt % to 30 wt % dicaprylyl carbonate.

Still referring to FIG. 1, the formulation comprises about 40 wt % to about 80 wt % the solvent, such as water. In some embodiments, the formulation comprises about 40 wt % to 50 wt %, about 50 wt % to 60 wt %, about 60 wt % to 70 wt %, or about 70 wt % to 80 wt % solvent water.

In any of the preceding embodiments, the formulation may further comprise a moisturizer, a humectant, a film-former, a surfactant, an additional solvent for the preservative or preservative system, or a combination of any two or more thereof.

Referring to FIG. 1, in some embodiments, the moisturizer is an Aloe barbadensis leaf extract. In some embodiments, the formulation comprises about 1.0 wt % to about 10.0 wt % moisturizer. In some embodiments, the formulation comprises about 1.0 wt % to about 2.0 wt %, about 2.0 wt % to about 3.0 wt %, about 3.0 wt % to about 4.0 wt %, about 4.0 wt % to about 5.0 wt %, about 5.0 wt % to about 6.0 wt %, about 6.0 wt % to about 7.0 wt %, about 7.0 wt % to about 8.0 wt %, about 8.0 wt % to about 9.0 wt %, or about 9.0 wt % to about 10 wt % moisturizer.

Referring still to FIG. 1, in some embodiments, the humectant is glycerin. In some embodiments, the formulation comprises about 1.0 wt % to about 20.0 wt % humectant. In some embodiments, the formulation comprises about 1 wt % to 5 wt %, about 5 wt % to 10 wt %, about 10 wt % to 15 wt %, or about 15 wt % to 20 wt % humectant.

Referring still to FIG. 1, in some embodiments, the film-former is maltodextrin. In some embodiments, the formulation comprises about 0.5 wt % to about 2.5 wt % film-former. In some embodiments, the formulation comprises about 0.5 wt % to 1.0 wt %, about 1.0 wt % to 1.5 wt %, about 1.5 wt % to 2.0 wt %, or about 2.0 wt % to 2.5 wt % film-former.

Referring still to FIG. 1, in some embodiments, the surfactant is selected from the group consisting of Disodium cocoamphodiacetate, Cocamide DEA, and the combination thereof. In some embodiments, the formulation comprises about 1.0 wt % to about 30.0 wt % surfactant. In some embodiments, the formulation comprises about 1 wt % to 5 wt %, about 5 wt % to 10 wt %, about 10 wt % to 15 wt %, about 15 wt % to 20 wt %, about 20 wt % to about 25 wt %, or about 25 wt % to about 30 wt % surfactant.

Referring still to FIG. 1, in some embodiments, the additional solvent for the preservative or preservative system is selected from the group consisting of Propylene Glycol, Methyl Propanediol, and the combination thereof. In some embodiments, the formulation comprises about 0.5 wt % to about 10.0 wt % additional solvent. In some embodiments, the formulation comprises about 0.5 wt % to 1.0 wt %, about 1 wt % to 2 wt %, about 2 wt % to 3 wt %, about 3 wt % to 4 wt %, about 4 wt % to 5 wt %, about 5 wt % to about 6 wt %, about 6 wt % to about 7 wt %, about 7 wt % to about 8 wt %, about 8 wt % to about 9 wt %, or about 9 wt % to about 10 wt % the additional solvent. In some exemplary embodiments, the formulation comprises about 0.5 wt % to 8 wt % solvent such as Propylene Glycol or about 0.5 wt % to about 10.0 wt % solvent such as Methyl Propanediol.

In a specific exemplary embodiment, the formulation includes an active pharmaceutical ingredient (API) in the form of zinc oxide, at least one rheology modifier in the form of a cross-linked corn starch, such as hydroxypropyl starch phosphate (Trade name: TEXTURLUX® RHEO, Tate & Lyle), and a solvent in the form of water. The formulation may further include at least one preservative or preservative system, at least one emulsifier, and at least one emollient. In a specific exemplary embodiment according to the foregoing, the emollient is beeswax.

In such embodiments, the hydroxypropylated starch phosphate is a cross-linked corn starch to act as a thickener and stabilizer for the emulsion. The hydroxypropyl starch phosphate gives the formulation a desirable viscosity. The starch is previously cooked and dried, allowing it to be added to the formulation to thicken it after emulsion. The presence of the starch in the formulation causes the formulation to become thixotropic, meaning the formulation becomes less viscous when mechanically stressed, allowing for smooth and comfortable application of the zinc oxide formulation to the patient's skin.

Applicator

Another aspect of the present disclosure relates to an applicator configured for delivering a formulation, such as the formulation described above. In various embodiments, the applicator is a cloth delivery device comprising a nonwoven cloth. In some implementations, the applicator may be made of a cloth that is formed to work particularly with the formulation of any foregoing embodiment, to further enable a smooth application to a patient's skin, as described above. In some embodiments, the applicator is a cloth made of polyethylene terephthalate (PET), polypropylene (PP), or a combination of both.

In various embodiments, the applicator is used to apply the formulation to a patient's affected area. The applicator configuration facilitates easy application with less mess for both the clinician and patient, and may provide a method for singled-handed formulation application to the patient. Furthermore, the applicator configuration provides a known unit dosage of the formulation (for example, four grams) so the clinician knows exactly how much formulation is being delivered, and it allows all of the formulation (i.e., the full dosage) to be transferred from the applicator to the patient (due in part to the non-permeability described below). In various implementations, the applicator could also be used as a wound dressing, where the clinician could attach the applicator to the patient on or adjacent to the patient's affected area. In some implementations, the applicator may be held to the patient using the zinc oxide formulation as an adhesive.

Figure 6:
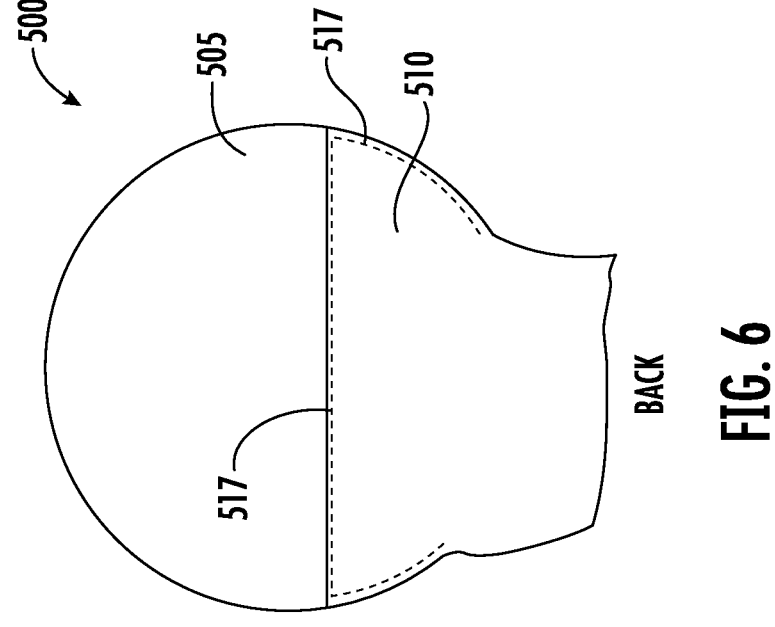
FIG. 6 shows a rear (user-facing) perspective view of the non-woven applicator of FIG. 5, according to an exemplary embodiment.

In various implementations, the applicator is a single-layered (FIG. 2) or multi-layered (FIGS. 5-6) sheet of material that is not permeable and thus would not be impregnable. Instead, the formulation would be disposed on an outwardly facing side of the applicator, for example, on an outwardly facing side of the applicator 200 shown in FIGS. 2-4, or applicator 500 shown in FIGS. 5-8. To prevent the applicator 200, 500 from absorbing the formulation, the applicator 200, 500 may be formed to have tightly punched fibers (i.e., creating a tight, dense cloth) and/or may comprise a calendared cloth that would prevent the formulation from migrating through the fibers of the applicator 200, 500. For example, the cloth may be calendared by exposing the cloth to a finishing process that would produce an effect such as higher luster, smoothness, or embossing. In various embodiments, the fiber material of the applicator 200, 500 would not be absorbent so that moisture remains within the formulation. In some embodiments, the applicator 200, 500 may have a finish (e.g., on the outermost sides) to improve usability, facilitate ease of formulation application, and/or facilitate patient comfort during application (e.g., softening finish, reduce absorbency, reduce linting, anti-microbial).

Table 2 provided below shows exemplary material types for use within the applicator 200, 500. The material and structures provided in Table 2 are exemplary only and should not be considered limiting. Other embodiments may include cellulose.

TABLE 2

| Fiber Composition | Fiber Bonding | Product Treatment | Thickness | Weight |
|---|---|---|---|---|
| 100% polyethylene terephthalate (PET) | Needlepunched | Calendared-1 side | 1.02 mm | 162 gsm |
| 100% polyethylene terephthalate (PET) | Needlepunched | Calendared-2 sides | 1.02 mm | 162 gsm |
| 100% polypropylene (PP) | Needlepunched | Calendared | 2.46 mm | 300 gsm |
| 90% PET/10% PP | Needlepunched | Calendared | 0.76 mm | 120 gsm |
| 100% polyethylene terephthalate (PET) | Spunlace | Flat | 1.13 mm | 100 gsm |

Figure 3:
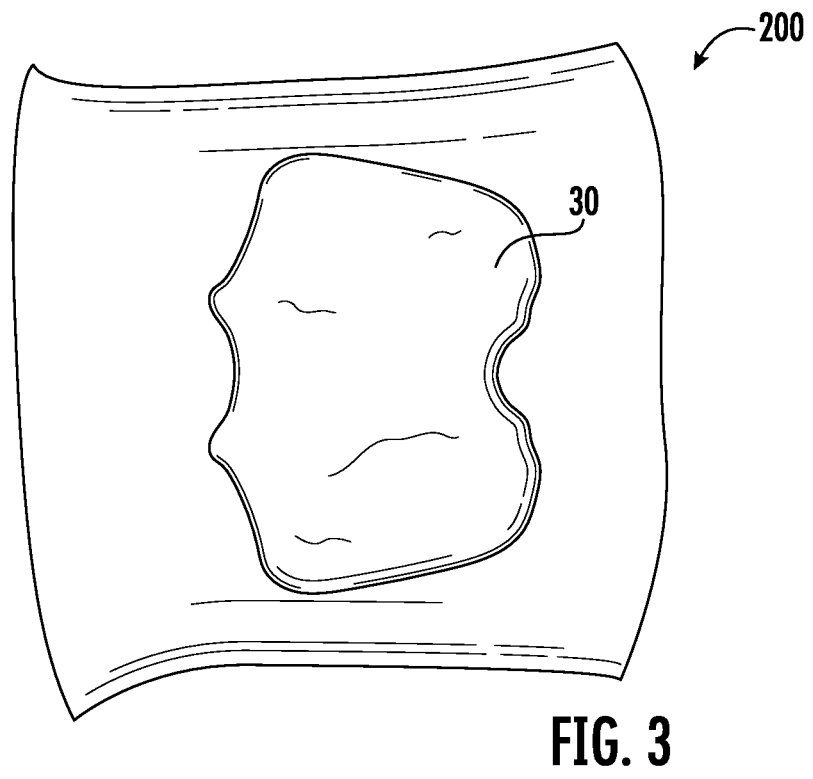
FIG. 3 shows a zinc oxide formulation on a cloth applicator, according to an exemplary embodiment.
Figure 4:
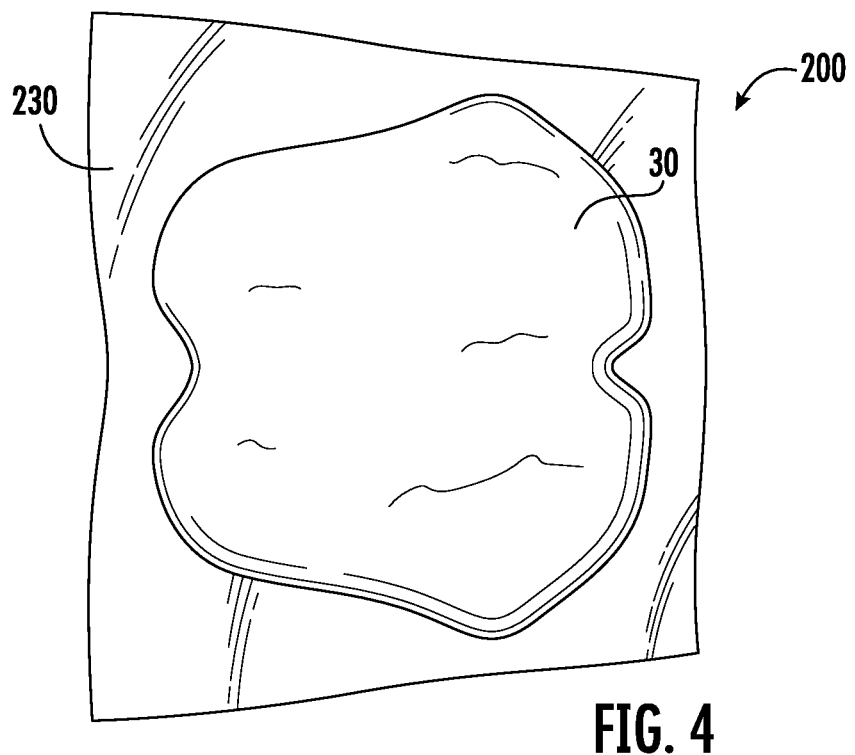
FIG. 4 shows a zinc oxide formulation on a cloth applicator, according to another exemplary embodiment.
Figure 5:
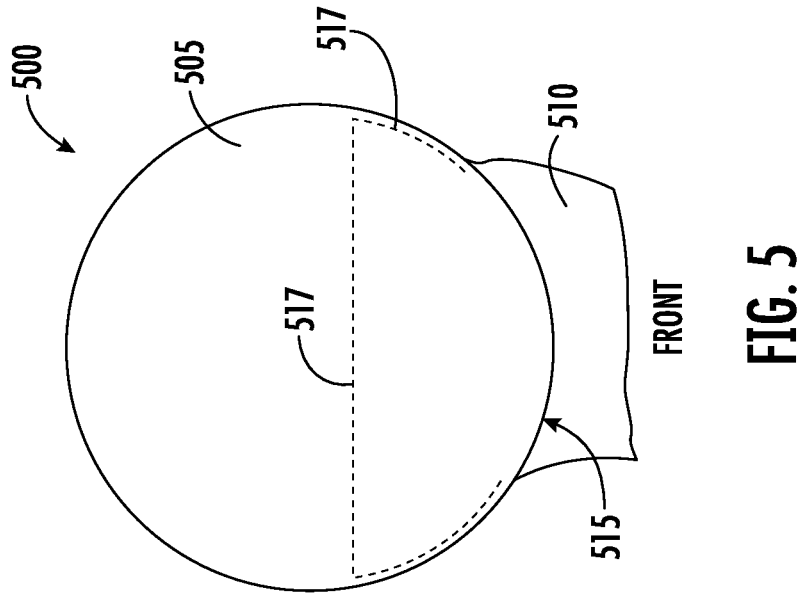
FIG. 5 shows a front (patient-facing) perspective view of a non-woven applicator having a pocket, according to an exemplary embodiment.
Figure 7:
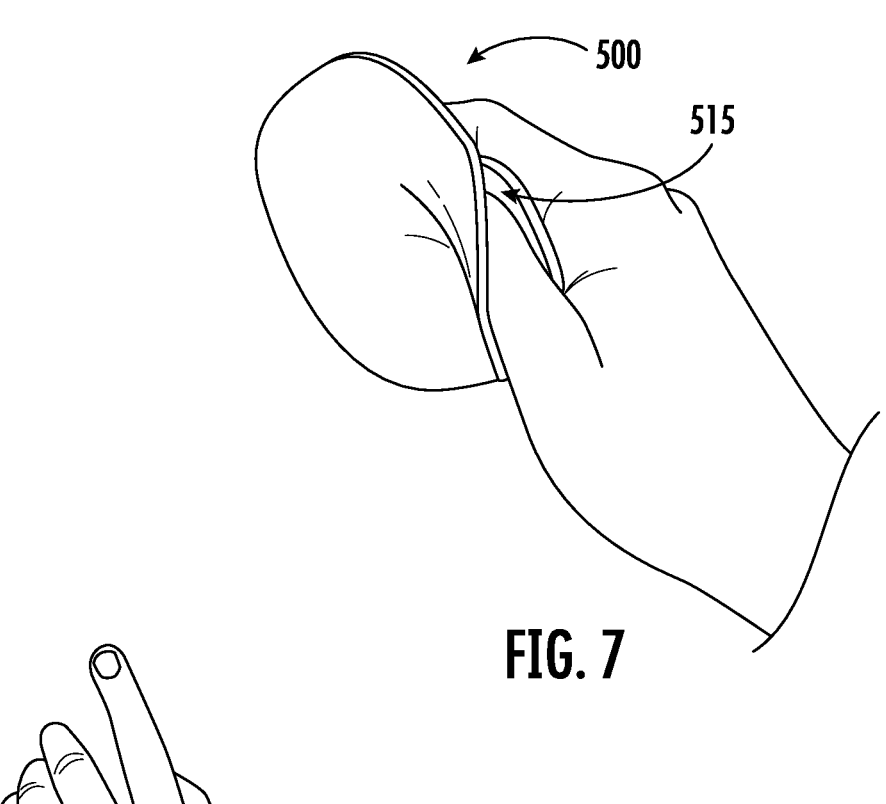
FIGS. 7-8 show alternate perspective views of the non-woven applicator of FIG. 5 during use, according to an exemplary embodiment.
Figure 8:
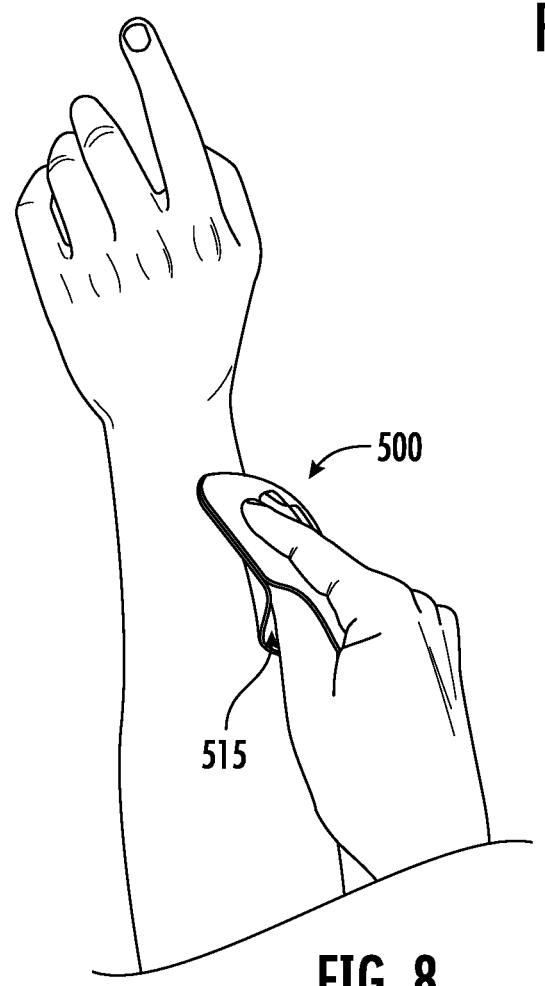

As shown in FIG. 3, in some embodiments, a dosage of the formulation 30 (for example, a weight of approximately four grams) will be placed in the center of the cloth applicator 200. The cloth may be folded in half (or another configuration) and the formulation 30 thereby spread out in such a way that the edges of the cloth remain formulation-free, allowing the clinician to grab a clean edge while removing the product from its packaging. Referring to FIG. 4, in some embodiments, the applicator 200 further includes a polyethylene or polypropylene film 230 attached to, laminated with, or otherwise incorporated into an outer facing layer of applicator 200 that prevents absorption of the zinc oxide formula into the cloth and aids in application on a patient's skin.

In an exemplary embodiment, the dimensions of the cloth applicator 200 is approximately 4 inches (+/−0.5 inch) by 4 inches (+/−0.5 inch) (or 10.16 cm by 10.16 cm, +/−1.27 cm in either dimension). In some implementations, the applicator 200 may be folded in a double parallel fold, an accordion fold, a quarter fold, a half-tri fold, a half-z fold, or in any other fold suitable to package and/or otherwise provide the applicator 200 for use.

Referring to the alternative embodiment of FIGS. 5-8, applicator 500 includes a pocket for a user's (e.g., clinician's) thumb. In various embodiments, applicator 500 is made of non-woven cloth as described above. As shown in FIG. 5-8, applicator 500 includes a first sheet 505, a second sheet 510 coupled to the first sheet 505, and a pocket 515 formed between the sheets 505, 510. In various embodiments, the sheets 505, 510 may be coupled at an interface 517 such that an interior of the pocket 515 is accessible at an open end of the applicator 500. In various embodiments, the applicator 500 may include more than two sheets (e.g., each similar or equivalent to the sheets 505, 510). In various embodiments, the applicator 500 further includes a film (not shown), as described above and shown in FIG. 4, that is coupled to either one or both sheets 505, 510, and may also contain a known unit dosage of the zinc oxide formulation (e.g., four grams) as shown and described with respect to FIGS. 3 and 4.

Packaging

In some embodiments, the applicator may be configured for a single use. In such embodiments, the applicator may be disposable and packaged such that a single applicator is disposed within a single package. In other embodiments, one or more applicators may be packaged in a single package, such as two, three, four, or five applicators in a package.

Figure 9:
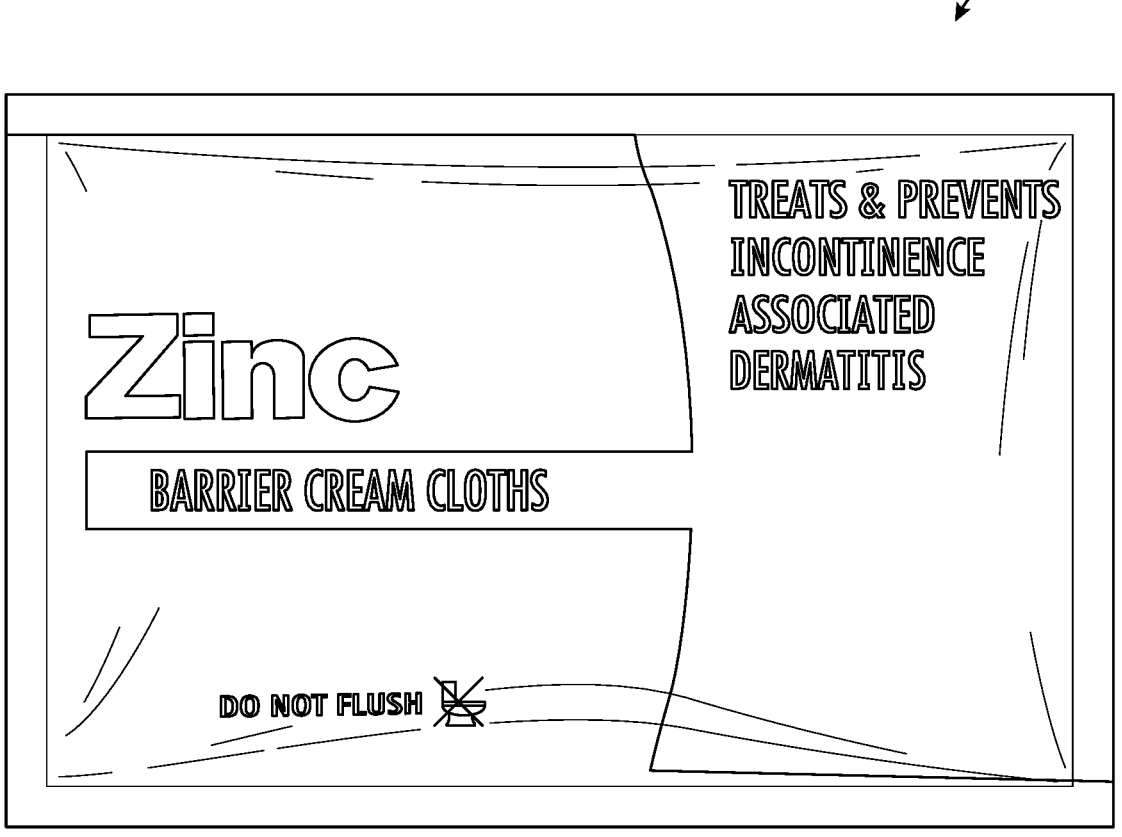
FIG. 9 shows a sealed pouch containing a non-woven applicator, according to an exemplary embodiment.

In various embodiments, the applicator is packaged in a single-use package 900, shown in FIG. 9. In an exemplary embodiment, the packaging is made of a tri-layer film, for example, comprising linear low-density polyethylene (LL-DPE), alumina oxide and polyethylene terephthalate. In an exemplary embodiment, the aforementioned film is folded in half and heat sealed on two edges and ultrasonically welded on the third edge. The ultrasonic weld may burn off any zinc oxide formulation present on the seal. In some embodiments, the package will have a tear notch which clinicians may use to open the package. In an exemplary embodiment, the inner dimension of a package 900 is approximately 4 inches (+/−1.0 inch) by 5.75 inches (+/−1.0 inch) (or 10.16 cm by 14.61 cm, +/−2.54 cm in either dimension).

Figure 10:
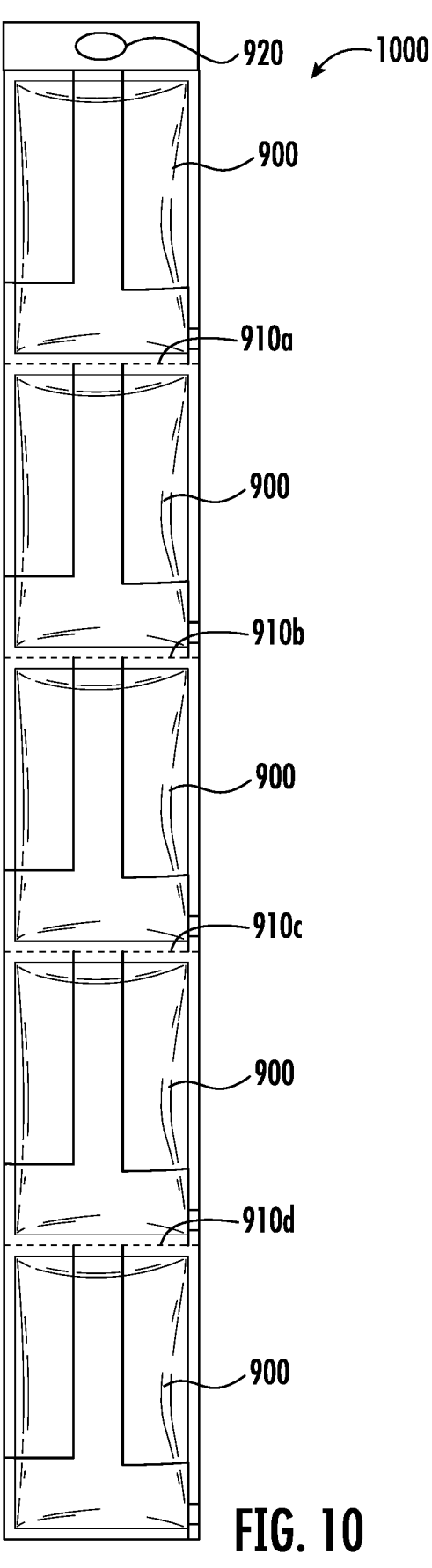
FIG. 10 shows a packaging configuration of a plurality of individual pouches of FIG. 9 connected in a sleeve, according to an exemplary embodiment.

The single-use packet 900 described above may be provided as individual packages or may be provided in a grouping of packages. In one packaging configuration, shown as configuration 1000 in FIG. 10, includes five single-use packets 900 attached into a sleeve with perforations 910a-910d between each single use packet 900 that allow the clinician to easily remove one pouch at a time. In this configuration, the clinician is able to visualize the quantity of product that has been used. In some embodiments, a hanger (e.g., an aperture 920 at the top of the sleeve) allows the product to be hung in a patient's room. In an exemplary embodiment, aperture 920 has a diameter of 0.75 inches (1.91 cm). Any number of single-use packages 900 may be provided in this configuration.

According to some embodiments, the perforations 910a-910d are all created to have equal strength (e.g., the "ties per inch" of the perforations are the same). In other embodiments, the strength of the perforations 910a-910d (e.g., ties per inch) differs. For example, the perforations are created to require more force to separate the top two packages from one another along perforations 910a than the force required to separate the packages along 910d. In this way, a user can easily remove the bottom-most package without pulling down and separating multiple packages. In an exemplary embodiment, perforation 910a is 2.50 ties per inch, perforation 910b is 1.75 ties per inch, perforation 910c is 1.25 ties per inch, and 910d is 0.75 ties per inch. The strength of the handing aperture 920 requires an even greater force to break to prevent the entire sleeve from being pulled down.

Figure 11:
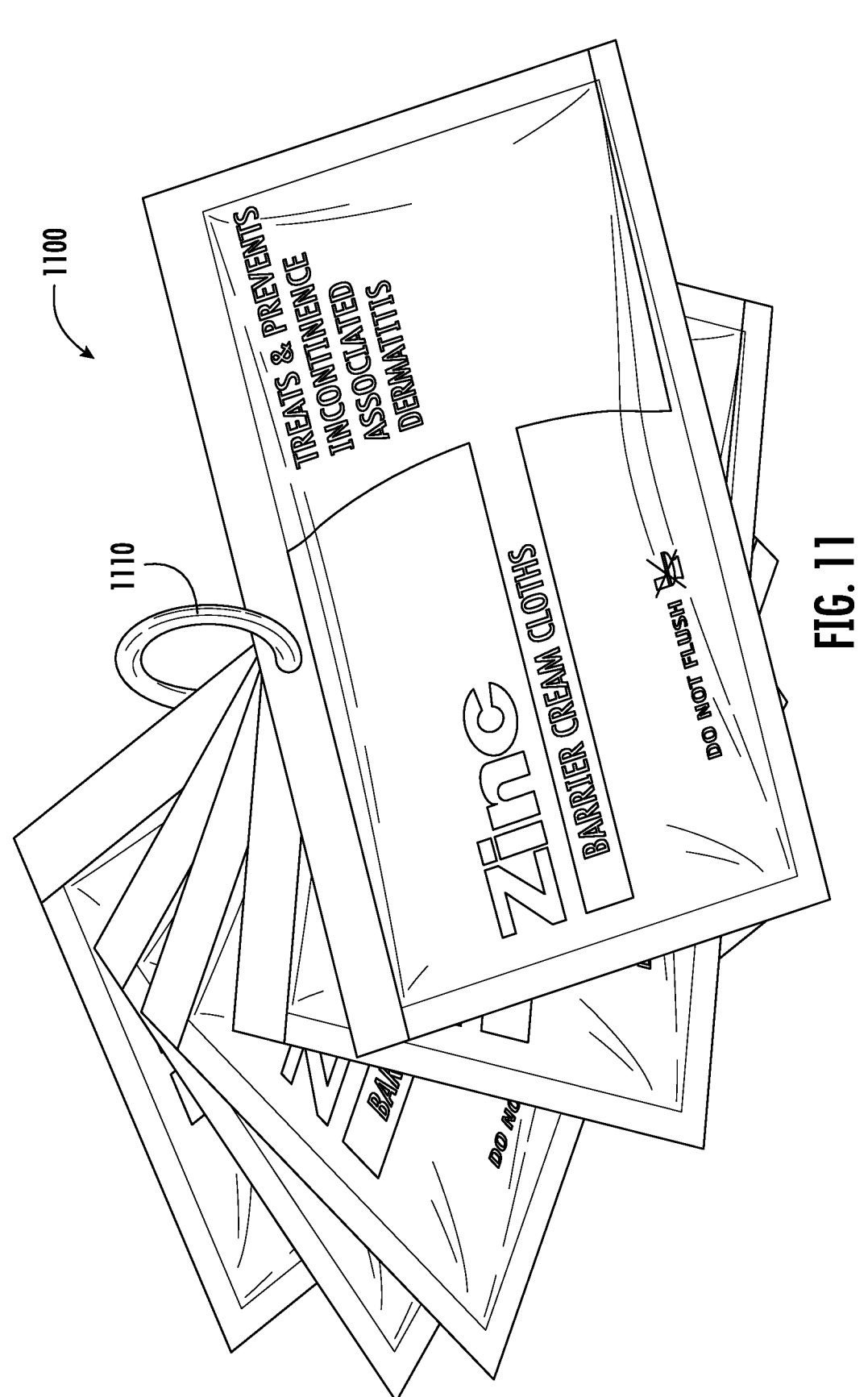
FIG. 11 shows another packaging configuration of a plurality of individual pouches of FIG. 10 hanging on a ring, according to an exemplary embodiment.

In an alternative packaging configuration, shown as configuration 1100 in FIG. 11, five single-use packets 900 hanging on a ring 1110. In some embodiments, each single-use packet 900 has a hole punch or other aperture 910 and, optionally, a perforation extending from the aperture 910 to the edge of the packet that allows the clinician to easily remove a packet 900 from the ring 1110 and visualize the quantity of product that has been used. Any number of single-use packages 900 may be provided in this configuration.

Method of Use

As described above, the applicator 200, 500 may be pre-packaged in a single use package, such as package 900 and/or may be pre-supplied with the formulation 10 (e.g., zinc oxide formulation). During use, the applicator 200 is removed from packaging 900 by the user (e.g., clinician). The formulation 10 is supplied to an outward facing side and the clinician holds the applicator 200, 500 to apply the formulation 10 to the affected area of the patient.

Notwithstanding the embodiments described above in reference to FIGS. 1-11, various modifications and inclusions to those embodiments are contemplated and considered within the scope of the present disclosure.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 elements refers to groups having 1, 2, or 3 elements. Similarly, a group having 1-5 elements refers to groups having 1, 2, 3, 4, or 5 elements, and so forth.

All patents, patent applications, provisional applications, and publications referred to or cited herein are incorporated by reference in their entirety, including all figures and tables, to the extent they are not inconsistent with the explicit teachings of this specification.

As utilized herein with respect to numerical ranges, the terms "approximately," "about," "substantially," and similar terms generally mean+/−10% of the disclosed values, unless specified otherwise. As utilized herein with respect to structural features (e.g., to describe shape, size, orientation, direction, relative position, etc.), the terms "approximately," "about," "substantially," and similar terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above.

It is important to note that any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A system comprising:
   an applicator for topical delivery of a zinc oxide formulation to an affected area on a patient, the applicator being a single layer sheet and having a first side and a second side opposite of the first side; and
   a film provided on an entirety of the first side, the film being non-permeable, unperforated, and comprising polyethylene or polypropylene;
   wherein the zinc oxide formulation is provided on the film.

2. The system of claim 1, wherein the applicator comprises polyethylene terephthalate (PET), polypropylene (PP), cellulose, or a combination thereof.

3. The system of claim 1, wherein the zinc oxide formulation comprises zinc oxide as an active pharmaceutical ingredient and one or more of a preservative or a preservative system, an emulsifier, a rheology modifier, an emollient, or water as a solvent.

4. The system of claim 1, wherein the applicator is calendared on the first side, the second side, or a combination thereof.

5. The system of claim 1, wherein the applicator comprises: (i) 100% polyethylene terephthalate (PET), (ii) 100% polypropylene (PP), or (iii) 90% PET and 10% PP.

6. The system of claim 3, wherein the zinc oxide formulation comprises about 5 wt % to about 25 wt % of the zinc oxide.

7. The system of claim 3, wherein;
   the zinc oxide formulation comprises the rheology modifier,
   the rheology modifier being hydroxypropylated starch phosphate, and
   the zinc oxide formulation comprises about 0.5 wt % to about 6.5 wt % of the hydroxypropylated starch phosphate.

8. The system of claim 3, wherein the emollient is selected from the group consisting of isopropyl palmitate, dicaprylyl carbonate, beeswax, lanolin, cetearyl ethylhexanoate, isopropyl myristate, dimethicone, and a combination thereof.

9. The system of claim 8, wherein the emollient is the beeswax and the zinc oxide formulation comprises about 0.5 wt % to about 6.0 wt % of the beeswax.

10. The system of claim 3, wherein the preservative is selected from the group consisting of phenoxyethanol, benzoic acid, dehydroacetic acid, ethylhexylglycerin, betulin, and a combination thereof.

11. The system of claim 3, wherein the emulsifier is selected from the group consisting of tri (polyglyceryl-3/lauryl) hydrogenated trilinoleate, glyceryl stearate, PEG-100 stearate, and a combination thereof.

12. The system of claim 3, wherein the zinc oxide formulation further comprises a moisturizer, a humectant, a film-former, a surfactant, an additional solvent for the preservative or the preservative system, or a combination thereof.

13. The system of claim 3, wherein the zinc oxide formulation comprises about 40 wt % to about 80 wt % of the water as the solvent.

14. The system of claim 1, wherein the zinc oxide formulation is provided in a unit dose of approximately 4 grams.

15. The system of claim 1, wherein the applicator is folded such that a portion of the first side is in confronting relation with another portion of the first side.

16. The system of claim 15, wherein the applicator is folded in half.

17. A package comprising:

the system of claim 1; and a film material folded in half and sealed along three open edges.

18. The package of claim 17, wherein the film material is tri-layer film comprising linear low-density polyethylene (LLDPE), alumina oxide, and polyethylene terephthalate.

19. The package of claim 17, wherein two of the three open edges are heat sealed and one of the three open edges is ultrasonically welded.

\* \* \* \* \*